US00PP15804P3

(12) United States Plant Patent
Lintott

(10) Patent No.: US PP15,804 P3
(45) Date of Patent: Jun. 21, 2005

(54) ***CHRYSANTHEMUM* PLANT NAMED 'PEACOCK ROYAL'**

(50) Latin Name: *Chrysanthemum morifolium*
Varietal Denomination: Peacock Royal

(75) Inventor: Keith G. Lintott, Bognor Regis (GB)

(73) Assignee: Cleangro Ltd., Chichester (GB)

( * ) Notice: Subject to any disclaimer, the term of this patent is extended or adjusted under 35 U.S.C. 154(b) by 0 days.

(21) Appl. No.: 10/692,912

(22) Filed: Oct. 24, 2003

(65) Prior Publication Data

US 2004/0083518 P1 Apr. 29, 2004

Related U.S. Application Data

(60) Provisional application No. 60/421,383, filed on Oct. 25, 2002.

(51) Int. Cl.[7] ..... A01H 5/00

(52) U.S. Cl. ..... Plt./293

(58) Field of Search ..... Plt./293

(56) References Cited

U.S. PATENT DOCUMENTS

PP10,213 P 1/1998 Wain ..... Plt./76
PP11,300 P 3/2000 Boeder ..... Plt./287

OTHER PUBLICATIONS

Royal Van Zanten Garden Mum Catalog 2002 listing *Chrysanthemum* variety 'Peacock VZ Royal' at pp. 9 and 11 (color picture) and 14.

*Primary Examiner*—Anne Marie Grunberg
*Assistant Examiner*—Annette H Para
(74) *Attorney, Agent, or Firm*—Howrey Simon Arnold & White LLP

(57) ABSTRACT

A new garden variety of *Chrysanthemum* plant named 'Peacock Royal' having a domed canopy of crimson decorative flowers and a slightly upright habit.

1 Drawing Sheet

Latin name of the genus and species: Botanical classification: *Chrysanthemum morifolium.*

Variety denomination: The new *Chrysanthemum* variety denomination is 'Peacock Royal.'

BACKGROUND OF THE INVENTION

The present invention comprises a new and distinct cultivar of *Chrysanthemum* botanically known as *Chrysanthemum morifolium,* and referred to by the cultivar name 'Peacock Royal.'

'Peacock Royal,' identified as 30279-2, originated from a whole plant mutation grown in a controlled planting of the patented variety 'Cleagar VZP1' (U.S. Plant Pat. No. 11,300) in Chichester, West Sussex, United Kingdom. The new variety 'Peacock Royal' has been asexually reproduced by vegetative cuttings in Chichester, West Sussex, United Kingdom and the distinguishing characteristics are retained through successive generations of asexual reproduction.

BRIEF SUMMARY OF THE INVENTION

'Peacock Royal' is a garden type of *Chrysanthemum* plant variety having a domed canopy of crimson decorative flowers and a slightly upright habit.

Comparison with Parent

Plants of the new *Chrysanthemum* variety 'Peacock Royal' are similar to the parent variety 'Cleagar VZP1' in plant habit and growth rate. In side-by-side comparisons in Chichester, West Sussex, United Kingdom, under commercial practice, plants of the new *Chrysanthemum* variety 'Peacock Royal' differed from plants of the parent 'Cleagar VZP1' in the following characteristic.

1. The new variety 'Peacock Royal' produces crimson flowers whereas the parent 'Cleagar VZP1' produces purple flowers.

Comparison with Other Varieties

Plants of the new *Chrysanthemum* variety 'Peacock Royal' are dissimilar to the variety 'Jenny Wren' (U.S. Plant Pat. No. 10,213) in plant habit and growth rate. In side-by-side comparisons in Chichester, West Sussex, United Kingdom, under commercial practice, plants of the new variety 'Peacock Royal' differed from 'Jenny Wren' in the following characteristics.

1. The new variety 'Peacock Royal' produces smaller flowers than 'Jenny Wren.'
2. The new variety 'Peacock Royal' has a more upright and less spreading habit than 'Jenny Wren.'

BRIEF DESCRIPTION OF ILLUSTRATION

Typical specimens of the plant and flowers for the new *Chrysanthemum* variety 'Peacock Royal' are shown in the accompanying digital photograph. The colors shown are as true as possible within the usual limits of this kind of illustration.

FIG. 1 is a whole plant view of the new variety 'Peacock Royal' grown in a pot. The plant shown in the illustration is 70 days from the commencement of planting outdoors in mid-June.

DETAILED BOTANICAL DESCRIPTION

The following description of the new *Chrysanthemum* variety 'Peacock Royal' is of plants grown outside, natural season, in Chichester, West Sussex, United Kingdom in the month of June. The cultivar has not been observed under all possible environmental conditions. The phenotype may vary significantly with variations in the environment such as temperature, length of day and light intensity, without any variance in genotype. The commercial classification of the new variety is a garden *Chrysanthemum.*

Plants of the new variety have been grown successfully under temperature conditions averaging about 50° F. at night and about 70° F. to 75° F. during the day under natural light conditions. The plants were grown outdoors in mid-June in 4 liter pots using a loamless compost. No growth retardants were used. To produce a commercial product the plants may be pinched once with the center bud removed. The typical container size for commercial growth is 4 liters (8"). It has been observed that the shelf life of the new variety is about 25 days with a response time of about 10 weeks natural season. The new variety is suitable for growth in a temperature range of 50° F. to 75° F.

The new variety may be produced as a pot plant. The following description is with respect to a plant produced as garden pot plant. In the description of this new *Chrysanthemum* variety, color values have been taken from The Royal Horticultural Society Colour Chart (R.H.S.C.C.).

PLANT

Plant type: Pot.
Habit: Domed — Round — Upright.
Height: 50 cm.
Width: 48 cm.
Branching characteristics: Free Branching — Slightly Curving.
Length of lateral branches: 30–40 cm.
Number of breaks from pinch: 5–7.
Stem color: Near 152C.
Response time: 70 days natural season.
Vigor: Medium/Tall.
Shelf life: 25 days.
Disease (susceptibility/resistance observed): None observed to date.
Pest (susceptibility/resistance observed): None observed to date.
Growth retardant type and treatment: No treatment necessary. The plants were grown for 10 weeks in natural season conditions.
Propagation:
*Type.*—Vegetative Propagation via Stem Cuttings.
*Time to rooting.*—12 days with soil temperatures of 70° F.
*Rooting habit.*—Fine and Fibrous.

FOLIAGE

Number of leaves per lateral branch: 12–13.
Compound or single: Single.
Arrangement of leaves: Alternate.
*Shape of leaf.*—Typically 5 lobed ovate.
*Size of leaf.*—Width (cm): 2–4 Length (cm): 5–7.
*Leaf apex.*—Acute.
*Base.*—Truncate.
*Attachment.*—Petioled.
*Aspect.*—Slightly undulating.
*Margin.*—Palmately Lobed.
*Surface characteristics.*—Top: Slightly Pubescent. Bottom: Slightly Pubescent.
Petiole:
*Color.*—Near 141B.
*Length.*—1.5–2.5 cm.
Venation: Net prominent mid vein at underside.
*Color.*—Upper side: near 141D. Under side: near 141D.
Color: Mature Leaf, upper side: near 138A; under side: near 138B Young Leaf, upper side: near 139B; under side: near 139B.

FLOWER

Flower appearance: Matte.
Flower type: Decorative.
Flower form: Slightly Incurving.
Flower shape: Round.
Flowering habit: Cyme.
Number of blossoms per branch: 7–8.
Inflorescence form: Corymibiform.
*Depth of fully expanded blossoms.*—2 cm.
*Diameter of fully expanded blossoms.*—4.5–5.5 cm.
Phyllaries:
*Number.*—18–20.
*Color.*—Near 137C.
*Length.*—5–8 mm.
*Width.*—1.5–2 mm.
*Texture/appearance.*—Slightly Pubescent.
Pedicel:
*Length.*—Terminal: 12 cm; lateral 8 cm.
*Color.*—Near 139C.
*Surface.*—Pubescent.
*Habit.*—Slightly Curving.
*Strength.*—Medium/Strong.
Ray florets:
*Form/shape.*—Straight.
*Texture/appearance.*—Matte.
*Number per flower.*—190–210.
*Length.*—1.5–2.5 cm; Width: 3–8 mm.
*Apex.*—Rounded/Slightly Dentate.
*Base.*—Tubular.
*Margin.*—Entire.
Disc florets: None observed.
Fragrance: None.
Flower bud (at onset of color):
*Length.*—1 cm.
*Diameter.*—1 cm.
*Form/shape.*—Globular.
General flower color:
1. *Ray florets, upper side.*—Immature: near 46A. Mature: near 45B. Older/Fading: near 47B.
2. *Ray florets, under side.*—Immature: near 46A. Mature: near 45B. Older/Fading: near 47B.
3. *Disc florets.*—None observed.
4. *Bud.*—Near 145B.

Flower progression with age: Flowers fade uniformly with age with some rolling of petals.

REPRODUCTIVE ORGANS

Gynoecium: Present on Ray florets.
Ray florets per individual flower:
*Pistil number.*—40–50 observed.
*Stigma color.*—Near 150C.
*Stigma shape.*—Forked.
*Style color.*—Near 150C.
*Style length.*—2–3 mm.
Androecium: Not observed.
Fruit and seeds: None observed.

What is claimed is:

1. A new and distinct variety of *Chrysanthemum* plant, substantially as described and illustrated herein.

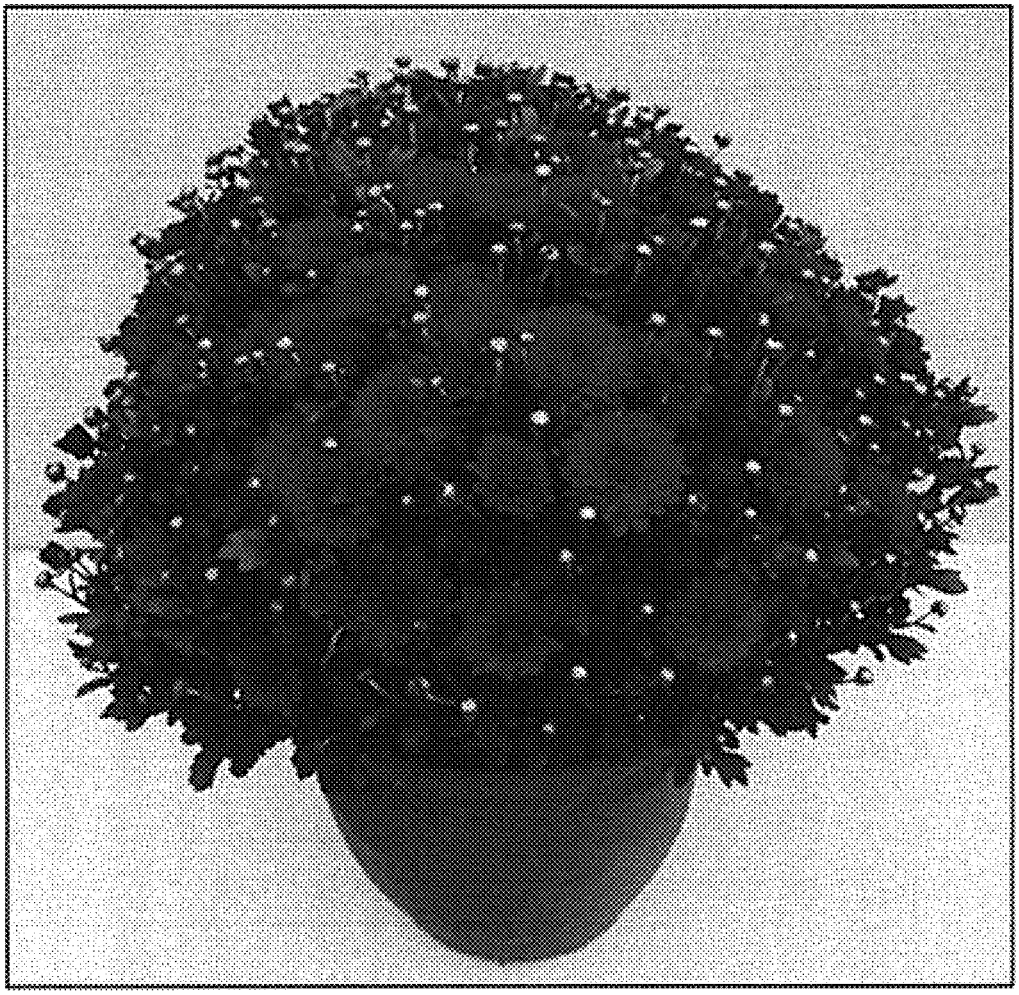

* * * * *